US00PP08072P

United States Patent [19]

van der Knaap

[11] Patent Number: Plant 8,072

[45] Date of Patent: Dec. 22, 1992

[54] CHRYSANTHEMUM PLANT—MYWAY CULTIVAR

[75] Inventor: Jacques C. M. van der Knaap, DeLier, Netherlands

[73] Assignee: Fides Beheer B.V., De Lier, Netherlands

[21] Appl. No.: 690,342

[22] Filed: Apr. 24, 1991

[51] Int. Cl.[5] ..... A01H 5/00

[52] U.S. Cl. ..... Plt./82.2

[58] Field of Search ..... Plt./74, 74.1, 82.2, Plt./82.1, 78

[56] References Cited

U.S. PATENT DOCUMENTS

P.P. 6,737 4/1989 van der Knaap ..... Plt. 74
4,616,099 10/1986 Sparkes ..... 47/58

OTHER PUBLICATIONS

Searle et al., 1968, "*Chrysanthemums the Year Round*", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of chrysanthemums", Euphytica, 15:156–162.

Dowrick et al., 1966, "The induction of mutations in Chrysanthemum using X-and gamma radiation", Euphytica, 15:204–210.

Gosling, ed., 1979, "*The Chrysanthemum Manual*—6th edition", The National Chrysanthemum Society, London, Essex Telegraph Press, Ltd. pp. 329–336.

Broertjes et al., 1978, *Application of Mutation Breeding Methods in the Improvement of Vegelatively Propagated Crops*, Elsevier Sci. Pub. Co. New York, pp. 162–175.

Broertjes et al., 1980, "A mutant of a mutant of a mutant of a . . . Irradiation of progressive radiation-induced mutants in a mutation breeding programme with *Chrysanthemum morifolium*," Euphytica 29:526–530.

*Primary Examiner*—Howard J. Locker

*Attorney, Agent, or Firm*—Burns, Doane, Swecker & Mathis

[57] ABSTRACT

A new and distinct cultivar of Chrysanthemum plant named Myway is provided. The new cultivar was the result of a mutation induced by controlled irradiation with x-rays and can be readily distinguished from the parent Broadway cultivar (U.S. Plant Pat. No. 6,737). More specifically, the new cultivar forms attractive yellow single flowers wherein the disc comprises a large dark brown central spot surrounded by a green border. The response period of the flowers is approximately nine weeks. The new cultivar is particularly suited for use in the production of a cut single spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium*, Ramat., and hereinafter is referred to by the cultivar name Myway.

The new cultivar is a mutation which was induced in a plant of the Broadway cultivar U.S. Plant Pat. No. 6,737) by irradiation with x-rays at a level of 1720 rads. The parent Broadway cultivar typically forms flowers wherein the ray florets are pale pink. The ability to produce the presently claimed mutation in a plant of the Broadway cultivar by any means was heretofore totally unknown and was incapable of prediction with certainty. The discovery of the new cultivar was made at De Lier, The Netherlands, during August, 1986.

It was observed that following the irradiation a single plant consistently formed flowers wherein the ray florets possessed a distinctive yellow coloration. Also, it was observed that the disc of the new cultivar comprised a larger central spot which was of a somewhat darker coloration than that of the parent Broadway cultivar. All other characteristics of the new plant were found to be substantially identical to those of the Broadway cultivar. Had I not discovered, carefully studied, and preserved this new cultivar, it would have been lost to mankind. This new cultivar is particularly well suited for growing in the production of a cut single or daisy spray.

It was found that the new cultivar of the present invention:

(a) exhibits attractive single flowers having an overall diameter of approximately 60 to 70 mm. wherein the ray florets are yellow and the disc comprises a large dark brown central spot surrounded by a green border,
(b) exhibits a flower response period of approximately nine weeks,
(c) forms dark green foliage, and
(d) has the ability to produce flowers of commercially acceptable quality throughout the year in a cut mum production program.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Myway has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Broadway parent (U.S. Plant Pat. No. 6,737), it is readily apparent that new cultivar possesses distinctive yellow ray florets while the Broadway cultivar consistently forms pale pink ray florets. Also, the spot which is present at the center of the disc of each flower tends to be larger and darker in coloration than that of the Broadway parent.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, during October, 1989. The plants described were grown under standard greenhouse conditions which approximate those commonly utilized for the production of cut mums.

Classification:

*Botanical.*—*Dendranthema morifolium* Ramat., cv. Myway.

*Commercial.*—Cut single spray.

Inflorescence

A. Capitulum:

*Form.*—When mature, flat to slightly cupped.

*Type.*—Single.

*Diameter across face.*—Approximately 60 to 70 mm. on average.

B. Corolla of ray and disc florets:

*Color (General tonality from a distance of three meters).*—Yellow.

*Color ray florets.*—Top surface — Yellow Group 12C. Under surface — Yellow Group 12D.

*Color disc florets.*—Greyed-Orange Group 165A as a central spot on the disc and Yellow-Green Group 147B at the periphery of the disc surrounding the central spot.

C. Reproductive organs:

*Androecium.*—Present in disc florets, numerous.

*Gynoecium.*—Present in both disc florets and ray florets, numerous.

Plant

A. General appearance:

*Height.*—Approximately 85 cm. on average.

B. Foliage:

*Color (upper surface).*—Yellow-Green Group 147A.

*Color (under surface).*—Yellow-Green Group 147B.

*Shape.*—Pinnately lobed.

I claim:

1. A new and distinct cultivar of Chrysanthemum plant named Myway, substantially as herein shown and described, which:

(a) exhibits attractive single flowers having an overall diameter of approximately 60 to 70 mm. wherein the ray florets are yellow and the disc comprises a large dark brown central spot surrounded by a green border, (b) exhibits a flower response period of approximately nine weeks, (c) forms dark green foliage, and (d) has the ability to produce flowers of commercially acceptable quality throughout the year in a cut mum production program.

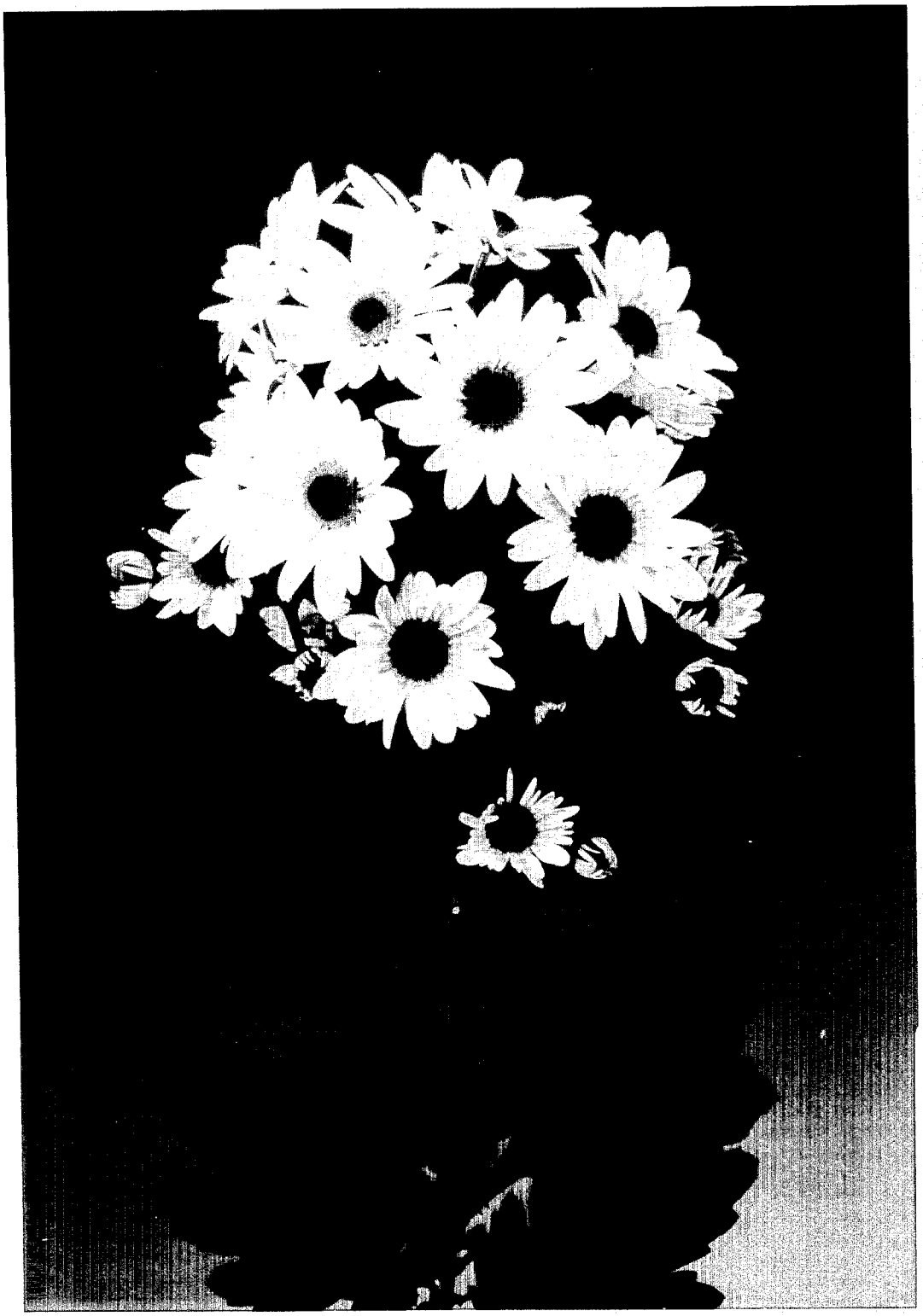

* * * * *